(12) United States Patent
Ghosh et al.

(10) Patent No.: US 8,768,459 B2
(45) Date of Patent: Jul. 1, 2014

(54) MORPHOLOGY-BASED PRECURSOR TO TEMPLATE MATCHING COMPARISON

(75) Inventors: Subham Ghosh, Blaine, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 28 days.

(21) Appl. No.: 13/561,967

(22) Filed: Jul. 30, 2012

(65) Prior Publication Data

US 2013/0053906 A1    Feb. 28, 2013

Related U.S. Application Data

(60) Provisional application No. 61/513,653, filed on Jul. 31, 2011.

(51) Int. Cl.
*A61N 1/00* (2006.01)

(52) U.S. Cl.
USPC ........ 607/4; 607/5; 607/19; 607/26; 600/515; 600/516; 600/518; 600/521

(58) Field of Classification Search
USPC .............. 607/4, 5, 19, 26; 600/515, 516, 518, 600/521
See application file for complete search history.

(56) References Cited

U.S. PATENT DOCUMENTS

| | | |
|---|---|---|
| 5,782,888 A | 7/1998 | Sun et al. |
| 6,393,316 B1 | 5/2002 | Gillberg et al. |
| 6,980,860 B2 | 12/2005 | Stadler et al. |
| 7,031,771 B2 | 4/2006 | Brown et al. |
| 7,062,322 B2 | 6/2006 | Stadler et al. |
| 7,130,677 B2 | 10/2006 | Brown et al. |
| 7,167,747 B2 | 1/2007 | Gunderson et al. |
| 7,242,978 B2 | 7/2007 | Cao et al. |
| 7,774,063 B2 | 8/2010 | Ghanem et al. |
| 7,826,893 B2 | 11/2010 | Cao et al. |
| 8,271,073 B2 | 9/2012 | Zhang et al. |
| 8,301,235 B2 | 10/2012 | Zhang et al. |
| 8,306,614 B2 | 11/2012 | Stadler et al. |
| 8,315,699 B2 | 11/2012 | Stadler et al. |
| 8,332,022 B2 | 12/2012 | Brown et al. |
| 8,391,964 B2 | 3/2013 | Musley et al. |
| 8,401,629 B2 | 3/2013 | Stadler et al. |
| 8,406,872 B2 | 3/2013 | Stadler et al. |
| 2011/0270110 A1 | 11/2011 | Zhang et al. |

*Primary Examiner* — Michael Kahelin
*Assistant Examiner* — Mallika D Fairchild
(74) *Attorney, Agent, or Firm* — Carol F. Barry

(57) ABSTRACT

One or more embodiments of the present disclosure relates to a method and/or system for classifying and/or treating heart rhythms. The present disclosure involves sensing electrical signals associated with depolarizations of a patient's heart. The sensed electrical signals are converted to digital values and storing the digital values. Normalizing solely a maximum and a minimum value of the stored digital values associated with a depolarization of the patient's heart without normalizing other stored digital values of the depolarization is another aspect of the present disclosure. The maximum and minimum values associated with the depolarization are compared to maximum and minimum values associated with a template derived from signals indicative of a heart depolarization of known type. A determination is made as to whether a match exists between the maximum and minimum values associated with the depolarization to the maximum and minimum values associated with a template.

30 Claims, 6 Drawing Sheets

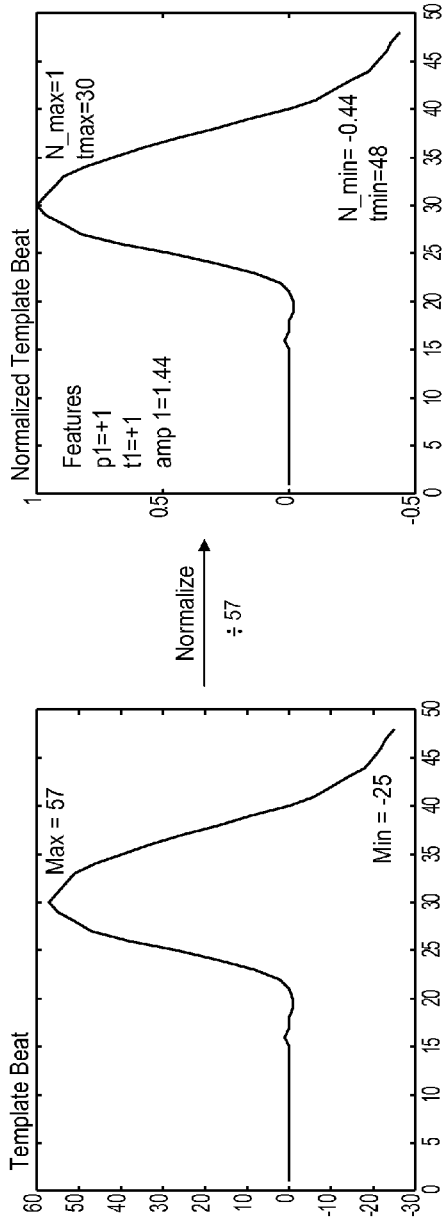
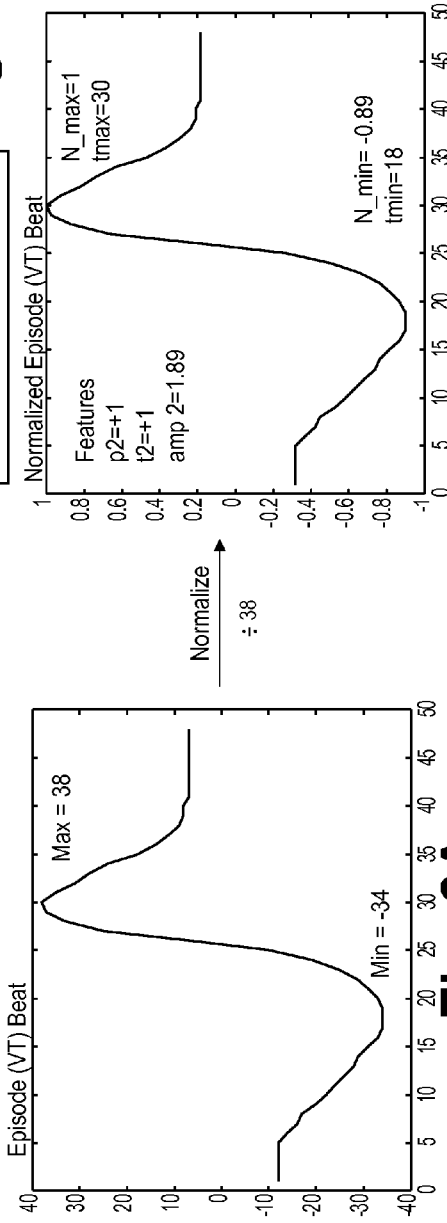

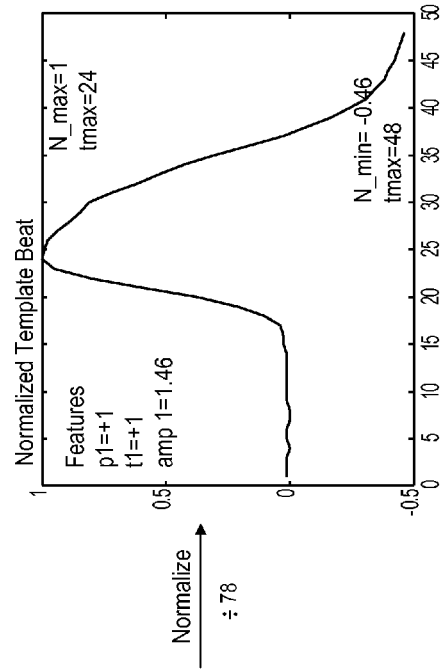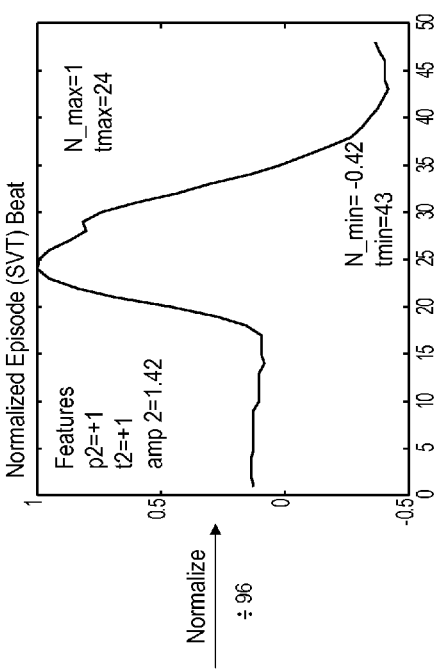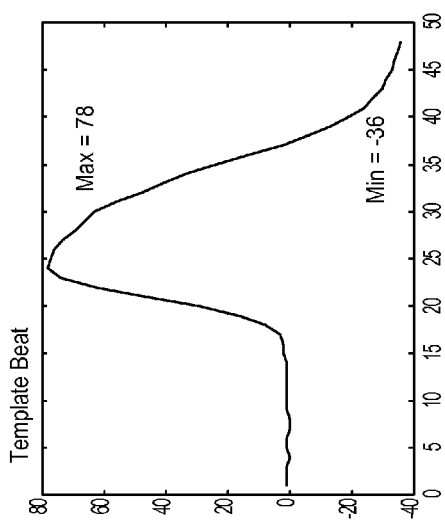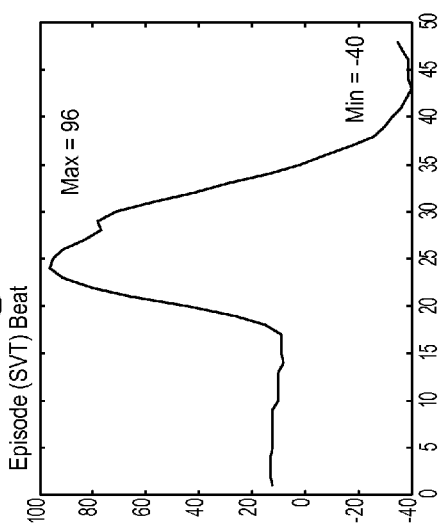

MORPHOLOGY-BASED PRECURSOR TO TEMPLATE MATCHING COMPARISON

CROSS-REFERENCE TO RELATED APPLICATIONS

This application claims the benefit of U.S. Provisional Application No. 61/513,653, filed on Jul. 31, 2011. The disclosure of the above application is incorporated herein by reference in its entirety.

TECHNICAL FIELD

The present disclosure relates to implantable monitors and stimulators generally and more particularly to implantable heart monitors and heart stimulators, such as implantable cardioverter/defibrillators (ICDs).

BACKGROUND

While implantable ICDs frequently deliver life saving therapy, occasionally an unnecessary electrical shock can be delivered to a patient's heart in response to rapid heart rates caused by exercise (e.g. sinus tachycardia) or by atrial fibrillation. Such rhythms, known collectively as supraventricular tachycardias (SVTs), may occur in up to 30% of ICD patients.

Anti-tachycardia pacing (ATP), a painless therapy, can be used to substantially terminate many monomorphic VTs without delivering unnecessary electrical shocks. While ATP is painless, ATP may not deliver effective therapy for all types of VTs. For example, ATP may not be as effective for polymorphic VTs, which is a fast rhythm (VTs) with variable morphologies. Polymorphic VTs and ventricular fibrillation (VFs) can be more lethal and require expeditious treatment by shock. The morphology of the QRS complex in the electrogram (EGM) signal may be used to discriminate a SVT episode from a VT episode or a monomorphic VT episode from a polymorphic VT or VF episode. Polymorphic VT and VF episodes have similar EGM morphology characteristics, and thus will be referred to interchangeably in this application. In the first case, the EGM morphology of each beat of an episode is compared to the morphology of a sample waveform recorded from the normal heartbeat, typically referred to as the template. In the second case, the morphology of each beat of a VT episode may be compared to that of one or more different beats from the same episode, which serve(s) as the template(s). One morphological method to discriminate between an episode beat and a template beat based on wavelet comparison. A template beat is either a normal beat or another beat from the same episode. An exemplary wavelet comparison method may be seen with respect to U.S. Pat. No. 6,393,316 issued May 21, 2002, and assigned to the assignee of the present disclosure. Generally, the wavelet comparison method involves aligning the EGM signal with the template signal based on certain characteristics (eg. peaks or valleys), transforming the digitized signal into signal wavelet coefficients, then identifying higher amplitude digitized signals of the signal wavelet coefficients. Thereafter, a match metric is generated that corresponds to the higher amplitude digitized signals of the signal wavelet coefficients. A corresponding set of template wavelet coefficients is derived from signals indicative of a heart depolarization of known type.

While the wavelet comparison method successfully eliminates or substantially reduces unnecessary electrical shocks delivered to a patient's heart, the wavelet comparison method requires shifting and alignment of the episode beat to the template beat for accurate morphologic discrimination. Shifting and alignment of the episode beat to the template beat may be computationally expensive, especially for monomorphic versus polymorphic VT discrimination in which more than one template beats derived from the same episode may be needed for comparison. Other template matching methods known in the art such as correlation, area of difference, etc. that could be used in place of the wavelet method are also computationally expensive. Thus, it may be beneficial to develop additional or alternative methods that are able to distinguish SVT from VT or monomorphic VT from polymorphic VT.

BRIEF DESCRIPTION OF DRAWINGS

FIG. 5A is a graph of a weighted template depolarization or template beat.

FIG. 5B is a graph of a normalized template depolarization or template beat.

FIG. 6A is a graph of a weighted VT depolarization or VT beat.

FIG. 6B is a graph of a normalized VT depolarization or VT beat.

FIG. 7A is a graph of a weighted template depolarization or template beat.

FIG. 7B is a graph of a normalized template depolarization or template beat.

FIG. 8A is a graph of a weighted template depolarization or template beat.

FIG. 8B is a graph of a normalized SVT depolarization or SVT beat.

DETAILED DESCRIPTION

The present disclosure quickly discriminates arrhythmia episodes when beats of a tachyarrhythmia episode are grossly different from the template beat or from a different depolarization cycle. In particular, the present disclosure uses simple feature-based morphologic comparison to determine whether a match exists between a template beat and an episodic beat. If the feature-based comparison determines the beats are dissimilar, it is unnecessary to perform a more detailed template matching routine or waveform correlation routine. Consequently, the present disclosure reduces the computational price and/or power expended in ICD/CRT-ICD devices in computing EGM morphology based template (e.g. using the wavelet method or other methods) match-percent scores for rhythm discrimination (e.g.

SVT versus VT discrimination or monomorphic VT versus polymorphic VT discrimination). While the wavelet method for template matching is used as the example in this disclosure, this invention applies equally for implantable systems utilizing other waveform template matching algorithms known in the art such as correlation, area of difference, etc.

One or more embodiments of the present disclosure relates to a method and/or system for classifying and/or treating heart rhythms. The present disclosure involves sensing electrical signals associated with depolarizations of a patient's heart. The sensed electrical signals are converted to digital values and storing the digital values. Normalizing solely a maximum and a minimum value of the stored digital values associated with a depolarization of the patient's heart without normalizing other stored digital values of the depolarization is another aspect of the present disclosure. The maximum and minimum values associated with the depolarization are compared to maximum and minimum values associated with a template derived from signals indicative of a heart depolarization of known type. A determination is made as to whether a match exists between the maximum and minimum values associated with the depolarization to the maximum and minimum values associated with a template. In response to only if determining the match between the depolarization and the template, a wavelet comparison is performed. A result of the wavelet comparison is used to select a therapy and deliver it to the patient.

Figure 1:
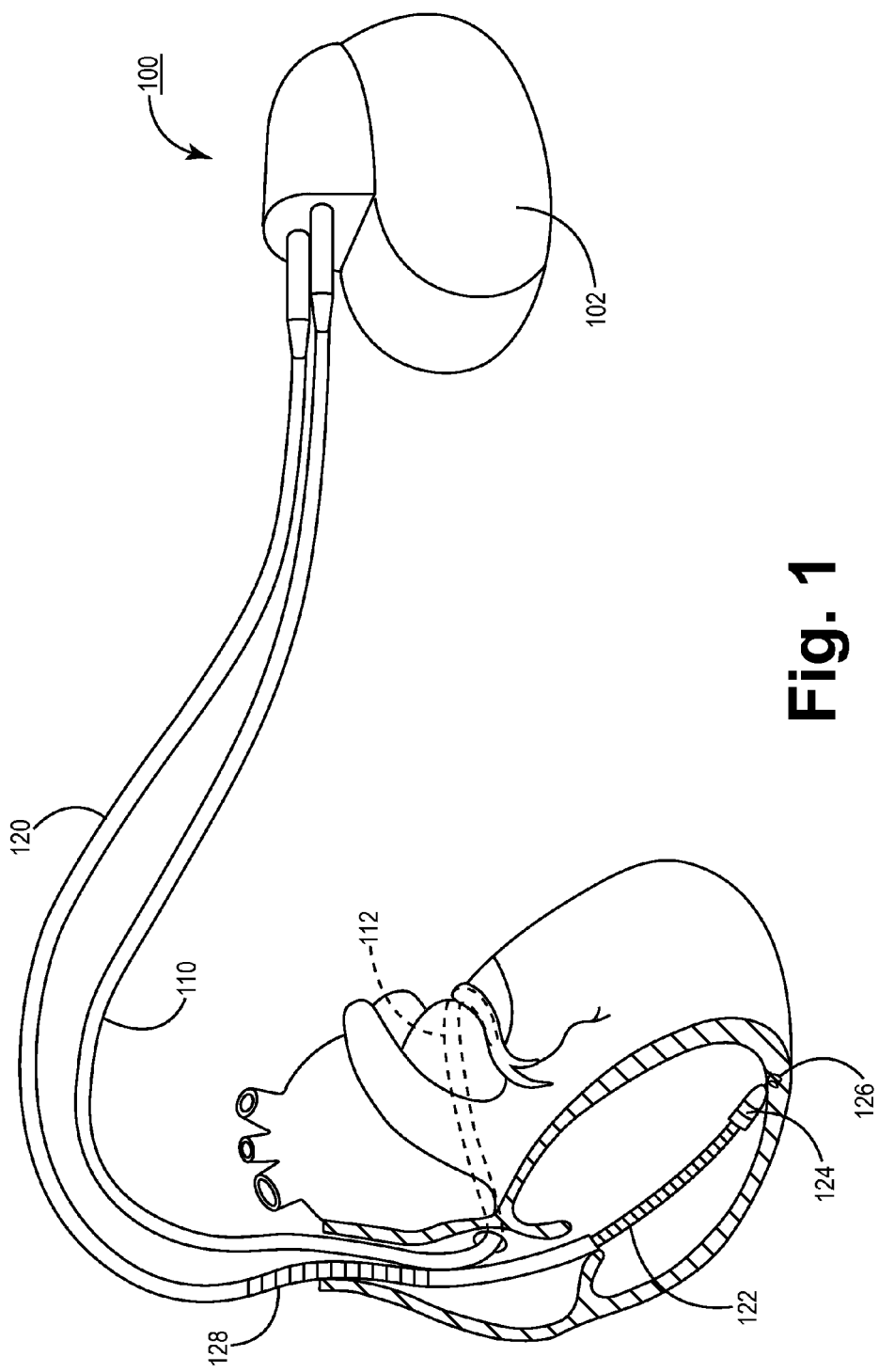
FIG. 1 is a schematic of a transvenous/subcutaneous electrode system in conjunction with a pacemaker/cardioverter/defibrillator embodying the present disclosure.

FIG. 1 illustrates an implantable pacemaker/cardioverter/defibrillator 100 and its associated lead system, as implanted in and adjacent to the heart. As illustrated, the lead system comprises a coronary sinus lead 110, a right ventricular lead 120, and a subcutaneous lead (not shown). The coronary sinus lead is provided with an elongated electrode located in the coronary sinus and great vein region at 112, extending around the heart until approximately the point at which the great vein turns downward toward the apex of the heart. The right ventricular lead 120 includes two elongated defibrillation electrodes 122 and 128, a ring electrode 124, and helical electrode 126, which is screwed into the tissue of the right ventricle at the right ventricular apex. The right ventricular lead 120 can be used to sense electrical signals (e.g. heart beats etc.) from the patient's heart. The housing 102 of defibrillator 100 may serve as an additional electrode.

In conjunction with the present disclosure, the lead system illustrated provides electrodes that may be used to detect electrical activity in the ventricles, for example, ring electrode 124 and tip electrode 126 may be used to detect the occurrence of an R-wave and ring electrode 124 and subcutaneous defibrillation electrode (not shown) may be used to provide an electrogram (EGM) signal (or sub-cutaneous or surface electrocardiogram signal) stored in response to R-wave detect. Onset of EGM signals that are stored begins when three intervals of abnormal arrhythmia is detected and stops storing when eight consecutive non-arrhythmia beats are detected. Alternatively, electrodes 124 and 126 may be used for both R-wave detection and as a source for the stored digitized EGM signal used for morphology analysis. In one or more embodiments, a far field EGM signal can be obtained. Other electrode configurations may also be employed. In alternative embodiments in which atrial depolarizations are of interest, sensing electrodes would correspondingly be placed in or adjacent the patient's atria.

In one or more other embodiments, a computer program can be configured to periodically store in memory sensed data (e.g. related to a sensed depolarization etc.). Computer instructions for storing data can be part of IMD's firmware or another computer program that is executed separately or integrated with computer instructions that are generally presented in the flow diagrams described herein.

Figure 2:
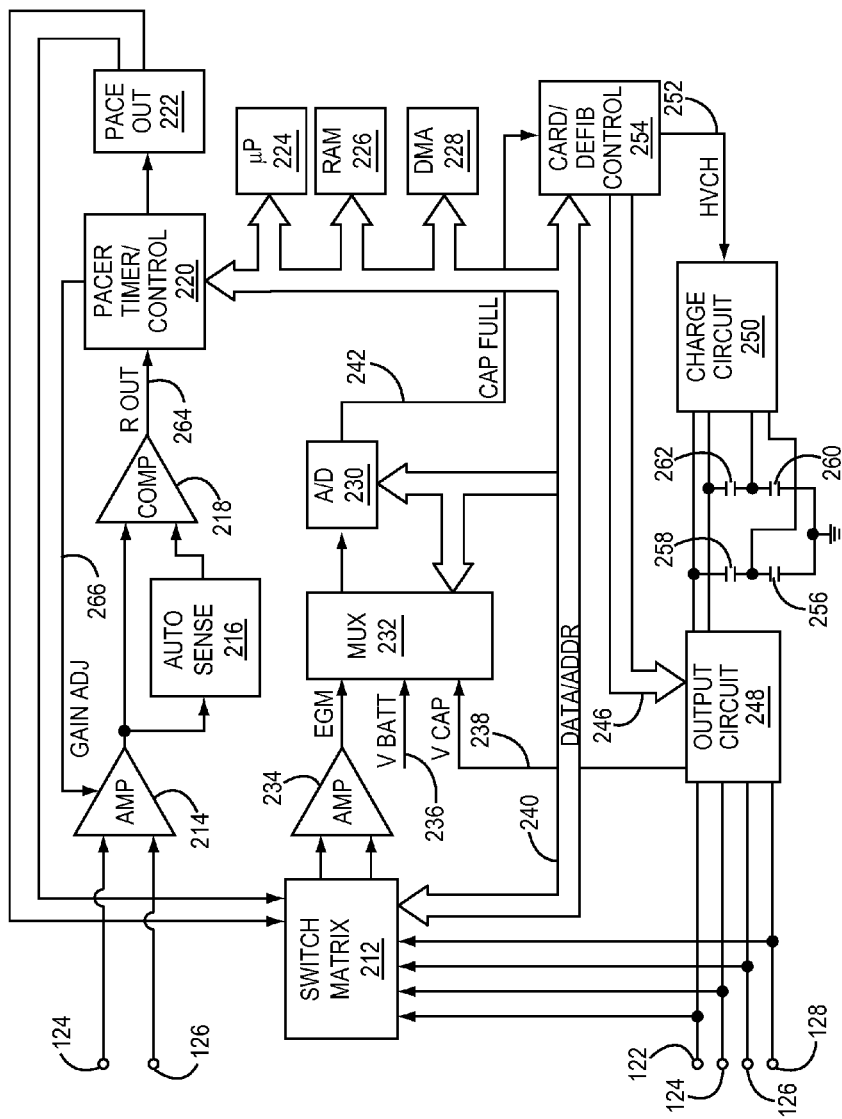
FIG. 2 is a functional schematic diagram illustrating the structure of one embodiment of an implantable pacemaker/cardioverter/defibrillator in which the present disclosure may be embodied.

FIG. 2 is a functional schematic diagram of an implantable/pacemaker/cardioverter/defibrillator in which the present disclosure may usefully be practiced. FIG. 2 is exemplary of the type of device in which the present disclosure may be embodied, and not as limiting, as it is believed that the present disclosure may usefully be practiced in a wide variety of device implementations, including devices having functional organization similar to any of the implantable pacemaker/defibrillator/cardioverters presently being implanted for clinical evaluation in the United States. The present disclosure is also believed practicable in conjunction with implantable pacemaker/cardioverters/defibrillators as disclosed in prior U.S. Pat. No. 4,548,209, issued to Wielders, et al. on Oct. 22, 1985, U.S. Pat. No. 4,693,253, issued to Adams et al. on Sep. 15, 1987, U.S. Pat. No. 4,830,006, issued to Haluska et al. on May 6, 1989 and U.S. Pat. No. 4,949,730, issued to Pless et al. on Aug. 21, 1990, U.S. Pat. No. 6,393,316, issued to Gillberg et al. on May 21, 2002 all of which are incorporated herein by reference in their entireties.

The device is illustrated as being provided with electrodes 122, 124, 126, 128. Electrodes 124 and 126 may be a pair of electrodes located in the ventricle shown in FIG. 1. Electrodes 122, 128 may correspond to the large surface area defibrillation electrodes located on the ventricular and coronary sinus leads illustrated in FIG. 1 or to epicardial or subcutaneous defibrillation electrodes. It is also appreciated that the housing 102 of the implantable pacemaker/cardioverter/defibrillator can be used as a remote electrode.

Electrodes 124 and 126 are shown as hard-wired to the R-wave detector circuit. The R-wave detector circuit comprises bandpass amplifier 214, auto-threshold circuit 216 for providing an adjustable sensing threshold as a function of the measured R-wave amplitude and comparator 218. A signal is generated on R-out line 264 whenever the signal sensed between electrodes 124 and 126 exceeds the present sensing threshold defined by auto threshold circuit 216. As illustrated, the gain on the band pass amplifier 214 is also adjustable by means of a signal from the pacer timing and control circuitry 220 on GAIN ADJ line 266.

The operation of this R-wave detection circuitry may correspond to that disclosed in U.S. Pat. No. 5,117,824 by Keimel, et al., issued Jun. 2, 1992, incorporated herein by reference in its entirety. However, alternative R-wave detection circuitry such as that illustrated in U.S. Pat. No. 4,819,643, issued to Menken on Apr. 11, 1989 and U.S. Pat. No. 4,880,004, issued to Baker et al. on Nov. 14, 1989, both incorporated herein by reference in their entireties, may also usefully be employed to practice the present disclosure.

The threshold adjustment circuit 216 sets a threshold corresponding to a predetermined percentage of the amplitude of a sensed R-wave, which threshold decays to a minimum threshold level over a period of less than three seconds thereafter, similar to the automatic sensing threshold circuitry illustrated in the article, "Reliable R-Wave Detection from Ambulatory Subjects", by Thakor et al., published in Biomedical Science Instrumentation, Vol. 4, pp 67-72, 1978, incorporated herein by reference in its entirety. An improved version of such an amplifier is disclosed in U.S. Pat. No. 6,249,701, issued Jun. 19, 2001 by Rajasekhar, et al., for an "Implantable Device with Automatic Sensing Adjustment", also incorporated herein by reference in its entirety. The present disclosure may also be practiced in conjunction with more traditional R-wave sensors of the type comprising a band pass amplifier and a comparator circuit to determine when the band-passed signal exceeds a predetermined, fixed sensing threshold.

Switch matrix 212 is used to select which of the available electrodes for use in conjunction with the present disclosure. For example, switch matrix 212 can switch electrode 124 and/or electrode 126 from sensing to deliver therapy. Additionally, switch matrix 212 can also select which electrode pair (e.g. electrode 122, 124 or electrodes 124, and 126) are employed in conjunction with R-wave width measurement function, which is controlled by the microprocessor 224 via data/address bus 240.

Signals from the selected electrodes are passed through band-pass amplifier 234 and into multiplexer 232, where they are converted to mult-bit digital signals by ND converter 230, for storage in random access memory 226 under control of direct memory address circuit 228. Microprocessor 224 employs the digitized EGM signal stored in random access memory 226 in conjunction with the morphology or signal analysis method of the present disclosure. For example, the microprocessor 224 may analyze the EGM stored in an interval extending from 100 milliseconds previous to the occurrence of an R-wave detect signal on line 264, until 100 milliseconds following the occurrence of the R-wave detect signal. The operation of the microprocessor 224 in performing the discrimination methods of the present disclosure is controlled by means of software stored in memory such as ROM, associated with microprocessor 224.

The remainder of the circuitry is dedicated to the provision of cardiac pacing, cardioversion and defibrillation therapies. The pacer timing/control circuitry 220 includes programmable digital counters which control the basic time intervals associated with VVI mode cardiac pacing, including the pacing escape intervals, the refractory periods during which sensed R-waves are ineffective to restart timing of the escape intervals and the pulse width of the pacing pulses. The durations of these intervals are determined by microprocessor 224, and are communicated to the pacing circuitry 220 via address/data bus 240. Pacer timing/control circuitry also determines the amplitude of the cardiac pacing pulses and the gain of band-pass amplifier, under control of microprocessor 224.

During VVI mode pacing, the escape interval counter within pacer timing/control circuitry 220 is reset upon sensing of an R-wave as indicated by a signal on line 264, and on timeout triggers generation of a pacing pulse by pacer output circuitry 222, which is coupled to electrodes 124 and 126. The escape interval counter is also reset on generation of a pacing pulse, and thereby controls the basic timing of cardiac pacing functions, including anti-tachycardia pacing. The duration of the interval defined by the escape interval timer is determined by microprocessor 224, via data/address bus 240. The value of the count present in the escape interval counter when reset by sensed R-waves may be used to measure the duration of R-R intervals, to detect the presence of tachycardia and to determine whether the minimum rate criteria are met for activation of the width measurement function.

Microprocessor 224 operates as an interrupt driven device, under control of software stored in the ROM associated with microprocessor 224 and responds to interrupts from pacer timing/control circuitry 220 corresponding to the occurrence of sensed R-waves and corresponding to the generation of cardiac pacing pulses. These interrupts are provided via data/ address bus 240. Any necessary mathematical calculations to be performed by microprocessor 224 and any updating of the values controlled by pacer timing/control circuitry 220 take place following such interrupts. These calculations include those described in more detail below associated with the discrimination methods of the present disclosure.

In the event that a tachycardia is detected, and an antitachycardia pacing regimen is desired, appropriate timing intervals for controlling generation of antitachycardia pacing therapies are loaded from microprocessor 224 into the pacer timing and control circuitry 220, to control the operation of the escape interval counter and to define refractory periods during which detection of an R-wave by the R-wave detection circuitry is ineffective to restart the escape interval counter. Similarly, in the event that generation of a cardioversion or defibrillation pulse is required, microprocessor 224 employs the counters to timing and control circuitry 220 to control timing of such cardioversion and defibrillation pulses, as well as timing of associated refractory periods during which sensed R-waves are ineffective to reset the timing circuitry.

In response to the detection of fibrillation or a tachycardia requiring a cardioversion pulse, microprocessor 224 activates cardioversion/defibrillation control circuitry 254, which initiates charging of the high voltage capacitors 256, 258, 260 and 262 via charging circuit 250, under control of high voltage charging line 252. The voltage on the high voltage capacitors is monitored via VCAP line 238, which is passed through multiplexer 232, and, in response to reaching a predetermined value set by microprocessor 224, results in generation of a logic signal on CAP FULL line 242, terminating charging. Thereafter, delivery of the timing of the defibrillation or cardioversion pulse is controlled by pacer timing/control circuitry 220. One embodiment of an appropriate system for delivery and synchronization of cardioversion and defibrillation pulses, and controlling the timing functions related to them is disclosed in more detail in U.S. Pat. No. 5,188,105, issued to Keimel on Feb. 23, 1993 and incorporated herein by reference in its entirety. However, any known cardioversion or defibrillation pulse generation circuitry is believed usable in conjunction with the present disclosure. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al., cited above, and in U.S. Pat. No. 4,375,817, issued to Engle et al., all incorporated herein by reference in their entireties may also be employed. Similarly, known circuitry for controlling the timing and generation of antitachycardia pacing pulses may also be used as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 7,726,380, issued to Vollmann et al. on Feb. 23, 1988 and U.S. Pat. No. 4,587,970, issued to Holley et al. on May 13, 1986, all of which are incorporated herein by reference in their entireties.

In modern pacemaker/cardioverter/defibrillators, the particular antitachycardia and defibrillation therapies are programmed into the device ahead of time by the physician, and a menu of therapies is typically provided. For example, on initial detection of tachycardia, an anti-tachycardia pacing therapy may be selected. On redetection of tachycardia, a more aggressive anti-tachycardia pacing therapy may be scheduled. If repeated attempts at anti-tachycardia pacing therapies fail, a higher-level cardioversion pulse therapy may be selected thereafter. Prior art patents illustrating such preset therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al. The present disclosure is believed practicable in conjunction with any of the known anti-tachycardia pacing and cardioversion therapies, and it is believed most likely that the invention of the present application will be practiced in conjunction with a device in which the choice and order of delivered therapies is programmable by the physician, as in current implantable pacemaker/cardioverter/defibrillators.

In the present disclosure, selection of the particular electrode configuration for delivery of the cardioversion or defibrillation pulses is controlled via output circuit 248, under control of cardioversion/defibrillation control circuitry 254 via control bus 246. Output circuit 248 determines which of the high voltage electrodes 122, 128 will be employed in delivering the defibrillation or cardioversion pulse regimen, and may also be used to specify a multielectrode, simultaneous pulse regimen or a multi-electrode sequential pulse regimen. Monophasic or biphasic pulses may be generated. One example of circuitry which may be used to perform this function is set forth in U.S. Pat. No. 5,163,427, issued to Keimel on Nov. 17, 1992, incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in the context of the present disclosure. Alternatively single monophasic pulse regimens employing only a single electrode pair according to any of the above-cited references that disclose implantable cardioverters or defibrillators may also be used.

As discussed above, switch matrix 212 selects which of the various electrodes are coupled to band pass amplifier 234. Amplifier 234 may be a band-pass amplifier, having a band pass extending for approximately 0.5 to 200 hertz. The filtered EGM signal from amplifier 234 is passed through multiplexer 232, and digitized in ND converter circuitry 230. The digitized EGM data is stored in random access memory 226 under control of direct memory address (DMA) circuitry 228. Preferably, a portion of RAM 226 is configured as a looping or buffer memory, which stores at least the preceding several seconds of the EGM signal.

The occurrence of an R-wave detect signal on line 264 is communicated to microprocessor 224 via data/address bus 240, and microprocessor 224 notes the time of its occurrence. If the morphology analysis function is activated, microprocessor 224 may, for example, wait 100 milliseconds or other physician selected interval following the occurrence of the R-wave detect signal, and thereafter transfer the most recent 200 milliseconds or other physician selected interval of digitized EGM stored in the looping or buffer memory portion of the random access memory circuit 226 to a second memory location, where the contents may be digitally analyzed according to the present disclosure. In this case, the transferred 200 milliseconds of stored EGM will correspond to a time window extending 100 milliseconds on either side of the R-wave detect signal. Window sizes in any case should be sufficient to allow analysis of the entire QRS complexes associated with the detected R-waves. The microprocessor 224 also updates software-defined counters that hold information regarding the beats that match a beat template. The counters are incremented on the occurrence of a match between a sensed beat and a template beat stored in memory. Skilled artisans appreciate that the template beat can be derived from signals indicative of a normal heart depolarization for a particular patient. In one or more other embodiments, template beat is determined for a particular population of patients. For example, a template beat may be an average heart beat experienced by a specified population of patients. Age, for example, may be a factor considered in determining an average heart beat.

The following exemplary arrhythmia discrimination methods described herein can be employed in commercially marketed Medtronic implantable devices or other suitable implantable pacemaker/cardioverter/defibrillators. To this end, the device determines whether sensed beats during a tachyarrhythmia episode matches a template beat and then associated software-defined counters track the numbers of beats that match template beats.

Figure 3:
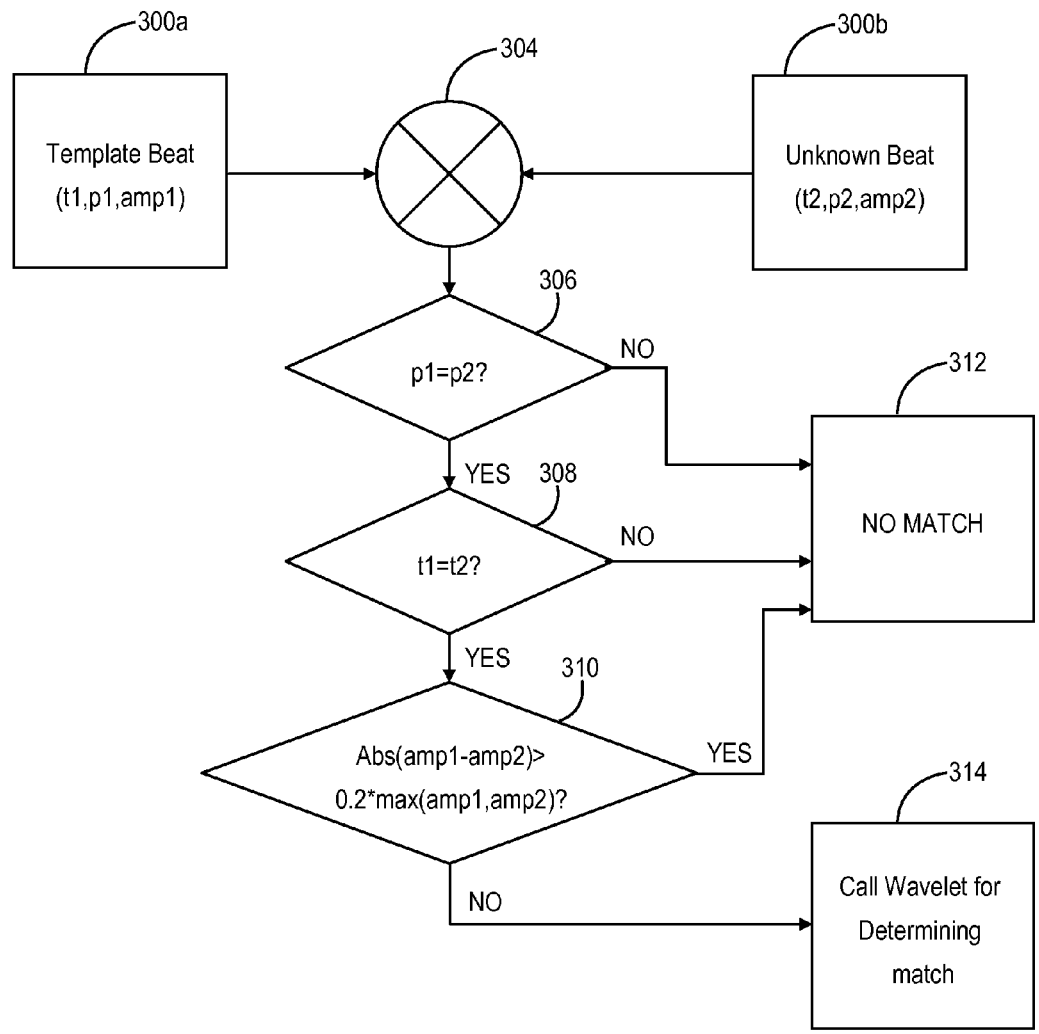
FIG. 3 is a functional flow diagram illustrating the over-all operation of tachyarrhythmia detection functions and their interrelation with the analysis function provided by the present disclosure, as embodied in a microprocessor based device as illustrated in FIG. 2.

FIG. 3 is a flow diagram that generally shows computer instructions, executed by a microprocessor, that can quickly and easily determine whether a certain cardiac condition (e.g. SVT, VT etc.) exists based solely upon comparing simple morphological features of an episodic beat to a template beat. More particularly, the discrimination method involves comparing gross morphological features between pairs of beats, in which one beat, referred to as a template beat, may be indicative of depolarization of a known type and the other beat belongs to a tachyarrhythmia episode. Gross morphological features of each beat may include, for example, a timing number (t) associated with a morphological feature of the beat, a peak number (p) related to a peak (i.e. q-R, R, qRs) or valley (i.e. (Q, QS, r-S) of the beat, normalized peak-to-peak amplitude (amp), and peak-to-peak amplitudes or a computationally simple mathematical function of one or more of these items. The timing number is based on a time associated with a maximum peak (tmax), time associated with a minimum peak or valley (tmin) and the order in which the timing number occurs (i.e. tmax<tmin or tmin<tmax).

A beat may be defined as the intracardiac electrogram signal within a pre-specified time window (e.g. 200 ms etc.). A beat is defined with respect to the time of sensing of ventricular depolarization corresponding to that beat. At block 300a, template beat data (also referred to as a first depolarization or a first beat) is stored into memory. The morphological features (t, p, amp) of this beat are labeled as t1, p1 and amp1 respectively. At block 300b, the episodic beat (also referred to as a second depolarization or a second beat) presently sensed through the medical electrical lead is also stored into memory. The corresponding morphological features (t, p and amp) for the second beat or episodic beat data are labeled as t2, p2 and amp2 respectively.

Figure 4:
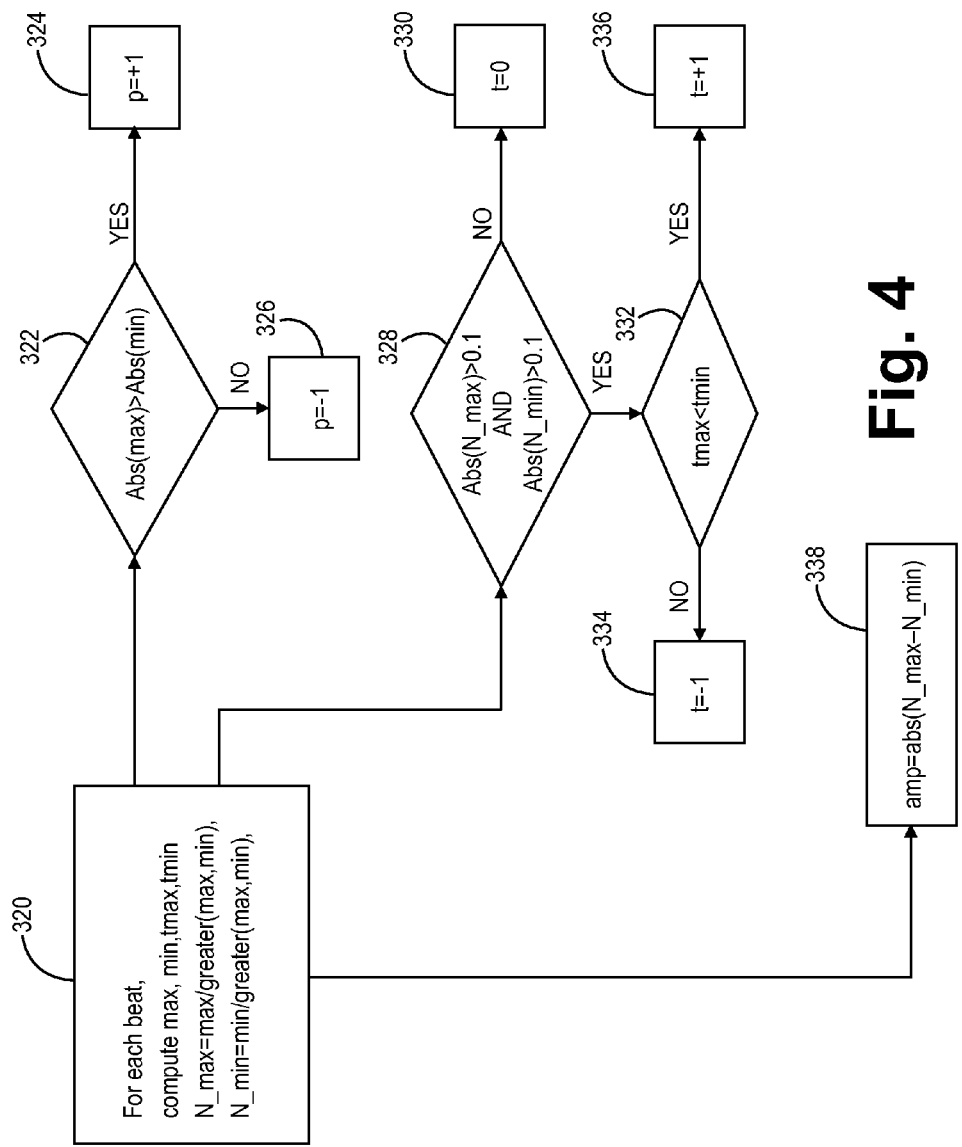
FIG. 4 is a flow diagram that relates to defining elements disclosed in FIG. 3.

At block 304, features of the episodic beat and/or the template beat are defined and stored in memory, which are used in determining whether three criteria, presented in blocks 306-310, establish a match between an episodic beat and a template beat. FIG. 4 provides details as to block 304. The exemplary flow diagram of FIG. 4 can be used to define parameters for determining the simple morphological features (t, p and amp) of each beat. For example, at block 320, numerous parameters are determined. Exemplary beat data parsed from a beat signal include its maximum amplitude (max), minimum amplitude (min), time of maximum amplitude, (tmax), time of minimum amplitude(tmin), normalized maximum amplitude computed as N_max=max/greater (abs (max),abs(min))max/greater(max,min), and normalized minimum amplitude N_min=min/greater(abs(max),abs (min)) derived from a weighted depolarization, where abs (max) and abs(min) represent the absolute unsigned magnitude of the max and minimum amplitudes respectively.

At block 322, the microprocessor 324 retrieves beat data from memory. For example, the absolute values of the maximum amplitude is compared to the absolute minimum value amplitude of the beat data. If the absolute value of the maximum amplitude is greater than the absolute value of the minimum amplitude, then p is set to +1.0 at block 324 and then stored into memory. In contrast, if the absolute value of the maximum amplitude is not greater than the absolute value of the minimum amplitude, then p is set to −1.0 at block 326 and then stored into memory.

At block 328, microprocessor 324 accesses the normalized data from a beat and determines the absolute value of normalized maximum peak which is compared to 0.10 and the absolute value of the normalized minimum data is also compared to 0.10. The computer instructions for block 328 is abs(N_max)>0.10 and abs(N_min)>0.10. The purpose of this step is to determine if either of the absolute values of the maximum and the minimum amplitudes is within the noise floor. If either of these values are less than the noise floor, then the morphological feature t is set to 0 at block 330 and stored into memory. If both the values are greater than noise floor, the YES path progresses to block 332. At block 332, tmax is compared to tmin. If tmax is less than tmin, then the NO path sets t=−1 at block 334. If tmax is greater than tmin, then the YES path sets t=+1 at block 336.

Another computation performed occurs at block 332 in which the normalized peak-to-peak amplitude (amp) of a beat is determined by taking the difference between the normalized maximum and minimum values. At block 338, the absolute value is taken of the difference between the normalized maximum and minimum values. After the parameters of the episodic beat and/or the template beat are defined, control of the computer program resumes to block 306 as shown in FIG. 3.

At block 306, a determination is made as to whether p1 is about equal to or substantially the same as p2. p1 is related to a morphological feature (e.g. peak, valley etc.) at a certain time of the template beat while p2 is related to a morphological feature at a certain time of the episodic beat. For example, p1 does not equal p2 if there is a valley (Q, QS, r-S) in the template beat and a peak (q-R, R, qRs) in the episodic beat or vice versa.

If p1 does not equal p2, then the NO path is followed to block 312 in which a determination is made that the episodic beat does not match the template beat. Lack of a match between the template beat and the episodic beat causes the control of the computer program to not call or execute the wavelet comparison method routine. Instead, the computer instructions can perform other actions. For example, the computer instructions can cause another template beat of another cardiac condition to be compared to the episodic beat(s) to determine whether a match exists and/or return to monitoring beats to compare to the first template.

If p1 does equal p2 at block 306, then the YES path is followed to block 308. At block 308, a determination is made as to whether another morphological feature (t) of the template beat equals that of the episodic beat. For example, a determination is made as to whether t1=t2. Essentially, t1=t2 if the order of timing of the peak and valley in the template beat is identical to that in the episodic beat. If t1 is not equal to t2, the order of timing of peak and valley in template beat is different from that in the episodic beat, thereby indicating that the beats are grossly different from each other.

If t1 does not equal t2, then the NO path is followed to block 312 in which a determination is made that the episodic beat does not match the template beat. If t1 does equal t2, then the YES path is followed to block 310.

Block 310 performs the comparison between another beat morphologic feature. For example, as noted in block 310, a computer instruction embodies the following criteria in which abs(amp1−amp2)>0.2*max(amp1,amp2). Specifically, the normalized peak to peak (p-p) amplitude(amp) of the first depolarization or beat (amp1) is subtracted from the normalized peak-peak amplitude associated with the second depolarization (amp2). Thereafter, a determination is made as to whether the absolute value of the difference in peak-to-peak amplitudes is greater than a predetermined threshold such as twenty (20) percent of the greater of the two peak-to-peak amplitudes being compared. The normalized peak-to-peak amplitude (amp) for each beat may be computed by simply subtracting the normalized minimum (N_min) from the normalized maximum (N_max), which were previously determined at block 320 in FIG. 4.

If it is determined that the relative difference between the normalized peak-to-peak amplitudes of the template beat and the episodic beat is greater than 20 percent, then the YES path is followed to block 312, which indicates that the template and episodic beats do not match. If the beats do not match, then the computer instructions cause the IMD to return to monitoring and/or use a different template related to another cardiac condition to determine whether a match can exist with the episodic beats by following the operations outlined in flow diagram for discriminating cardiac conditions as depicted in FIG. 3.

If it is determined that the relative difference between the amplitude of the template beat and the episodic beat is less than 20 percent, then the NO path is followed to block 314. At block 314, the wavelet comparison algorithm is executed using episodic beat data to verify whether a match exists between the template and episodic beats.

Examples are presented below to show application of the SVT rejection algorithm. The SVT rejection algorithm is used as a precursor to a wavelet comparison method or waveform correlation routine. An exemplary wavelet comparison method may be seen with respect to U.S. Pat. No. 6,393,316 issued May 21, 2002, and assigned to the assignee of the present disclosure, the disclosure of which is incorporated by reference in its entirety herein. As a precursor, the SVT rejection algorithm can be used to eliminate the full wavelet comparison method described in U.S. Pat. No. 6,393,316. The SVT rejection algorithm quickly and easily discriminates between whether a patient is experiencing SVT versus VT. In particular, the SVT rejection algorithm substantially reduces the number of clock cycles consumed in order to determine whether a patient exhibits SVT or VT as compared to the wavelet comparison method.

FIGS. 5A-6B depict an example of an SVT rejection algorithm in which the algorithm is used to determine whether morphological features of a template beat matches an episodic beat. If morphological features of a template beat do not match an episodic beat, computer instructions stored in memory instruct the microprocessor 324 to skip or do not call and perform the full wavelet analysis routine between the template beat and the episodic beat.

FIG. 5A depicts a weighted VT template depolarization in which the y-axis is amplitude and the x-axis is time-samples in which a sampling rate of 256 hertz (Hz) is employed. A maximum peak has amplitude of 57 whereas the minimum peak has an amplitude of −25 for the weighted template depolarization.

The weighted template depolarization undergoes a normalization process in order to obtain a normalized template beat as shown in FIG. 5B. For example, data from the weighted template depolarization is divided by largest absolute value of the maximum or minimum peak. In this example, maximum peak of 57 is larger than minimum peak of 25; therefore, the data from the weighted template depolarization is divided by 57, which provides normalized data along the y axis of FIG. 5B. As shown, the y-axis extends from −0.50 to 1.0 along with 0.5 intervals.

Using the equations listed above, the normalized template beat data include p1=+, t1=+1, amp1=1.44, N_max=1, tmax=30, N_min=−0.44, tmin=48 in which "max" relates to the maximum amplitude and "min" relates to minimum amplitude data. p is an indicator for the dominance of magnitudes of maximum versus minimum amplitude. If the minimum amplitude (i.e. a valley) has a magnitude that dominates the magnitude of the maximum (i.e. a peak), then p=+1. If the maximum amplitude (i.e. peak) has a magnitude that dominates the magnitude of the minimum (i.e. a valley), then p=−1.

t is indicative of yet another gross morphological feature. For example, tmax or tmin may be employed to normalize the data and then the comparison of the tmax to tmin assists in determining the relative timing. Specifically, tmax or tmin determines if either of the maximum or minimum amplitude is within noise floor in which case t=0, or if the timing (tmax) of the maximum (i.e. a peak) precedes (t=+1) or follows (t=−1) the timing (tmin) of the minimum (i.e. a valley). Ratios of the maximum value and minimum value, respectively, are made to determine whether either the maximum value and minimum value exceed a predetermined threshold such as 0.10, as shown in block 320. In particular, N_max=max/greater(abs(maximum),abs(minimum)) and N_min=min/greater(abs(maximum),abs(minimum)). If both these quantities are greater than the threshold, then a determination is made as to whether tmax is less than tmin. tmax and tmin are the times of peak (maximum) and valley(minimum), respectively. If tmax is less than tmin, then the feature t is set to t=+1; otherwise, t is set to t=−1. Therefore, the ratio, explained above, performs the normalization of the peak and the valley. If the absolute values of both exceed a certain threshold indicative of noise floor, the comparison of the tmax to tmin is performed to determine the relationship between timings of the peak and the valley of the beat.

The weighted episodic beat is shown in FIG. 6A has a maximum peak 38 and a minimum peak at 34. Since the absolute value of the minimum and maximum peaks is 38, the data from the weighted episodic beat is divided by 38. The resultant normalized episodic beat is shown in FIG. 6B. Features of the normalized episodic beat are determined as p2=+1, t2=−1, amp2=1.89, N_max=1, tmax=30, N_min=−0.89, and tmin=18. Since t1≠t2, the template beat does not match the episodic beat. Therefore, the wavelet comparison method routine is not called.

The second example, presented in FIGS. 7A-8B, reveals substantial similarity exists between simple morphologic features associated with the template beat and episode beats. Similarity of the template beat to the episodic beat is verified by more detailed template matching between the two beats such as through the wavelet comparison method.

Referring to FIG. 7A, a weighted SVT template depolarization is shown in which the y-axis is amplitude and the x-axis is time samples (sampling rate 256 Hz). A maximum peak has amplitude of 78 whereas the minimum peak has an amplitude of −36 for the weighted template depolarization.

The weighted template depolarization undergoes a normalization process in order to obtain a normalized template beat as shown in FIG. 7B. For example, data from the weighted template depolarization is divided by largest absolute value of the maximum or minimum peak. In this example, maximum peak of 78 is larger than minimum peak of −36; therefore, the data from the weighted template depolarization is divided by 78, which provides normalized data along the y axis of FIG. 5B. As shown, the y-axis extends from −0.50 to 1.0 along with 0.5 intervals therebetween.

Using the equations listed above, the normalized template beat data include p1=+1, t1=+1, amp1=1.46, N_max=1, tmax=24, N_min=−0.46, tmin=48. p is an indicator for the dominance of magnitudes of maximum versus minimum amplitude. If the minimum amplitude (i.e. valley) has a magnitude that dominates the magnitude of the maximum (peak), then p=+1. If the maximum amplitude (i.e. peak) has a magnitude that dominates the magnitude of the minimum (i.e. valley), p=−1. As previously stated, t is indicative of another gross morphological feature. t can be used to determine if either of maximum or minimum amplitude is within noise floor in which case t=0, or if the timing (tmax) of the maximum (peak) precedes (t=+1) or follows (t=−1) the timing (tmin) of the minimum (valley). Therefore, the ratio, explained above, assists in normalizing the data and then the comparison of the tmax to tmin assists in determining the relative timing.

The weighted episodic beat is shown in FIG. 8A has a maximum peak 96 and a minimum peak at −40. Since the greater of the absolute value of the minimum and maximum peaks is 96, the data from the weighted episodic beat is divided by 96. The resultant normalized episodic beat is shown in FIG. 8B. Features of the normalized episodic beat are determined as p2=+1, t2=+1, amp2=1.42, N_max=1, tmax=24, N_min=−0.42, and tmin=43. Additionally, abs(amp1−amp2)=0.04, 0.2*max(amp1, amp2)= 0.2*1.46=0.292, abs(amp1−amp2)<0.2*max(amp1,amp2). Since t1=t2, the template beat matches the episodic beat. Therefore, the wavelet comparison method routine is called in order to verify the match and to determine the cardiac condition that exists.

As shown by the examples and the flow diagram presented in FIG. 3, the present disclosure determines types of heart rhythms by comparing pairs of beats or depolarizations without shifting and aligning the normalized digital values associated with the pairs. The present disclosure uses simple feature-based morphologic comparison to determine whether a match exists between a template beat and an episodic beat. If the feature-based comparison determines the beats are dissimilar, it is unnecessary to perform a more detailed template matching routine or waveform correlation routine. Consequently, the present disclosure reduces the computational price and power expended in implantable devices such as subcutaneous monitors and ICD/CRT-ICD devices in computing wavelet (or other template matching methods) match-percent scores for rhythm discrimination. A more detailed description of a method to discriminate SVT from VT is described in a co-pending U.S. patent application Ser. No. 61/513,649 and co-pending patent application Ser. No. 13/562,039 filed by Subham Ghosh et al. on the same day as the present application, the disclosure of which is incorporated herein in its entirety. Accordingly, the present disclosure provides an alternative method of easily and reliably determining a type of heart rhythm. In one or more other embodiments, the teachings of the present disclosure can be implemented in devices such as the Medtronic, Inc. Reveal or a Reveal-like subcutaneous device that perform rhythm classification but do not deliver therapy. For example, the disclosure as embodied in FIGS. 3-8B may be implemented by a monitoring device such as Medtronic's Reveal device. Various examples of this disclosure have been described. These and other examples are within the scope of the following claims.

The invention claimed is:

1. A method of treating heart rhythms, comprising:
  sensing electrical signals associated with depolarizations of a patient's heart;
  converting the sensed electrical signals to digital values and storing the digital values;
  normalizing solely a maximum and a minimum value of the stored digital values associated with a depolarization of the patient's heart without normalizing other stored digital values of the depolarization;
  comparing the maximum and minimum values associated with the depolarization to maximum and minimum values associated with a template derived from signals indicative of a heart depolarization of known type or from a different depolarization cycle;

determining if a match exists between the maximum and minimum values associated with the depolarization to the maximum and minimum values associated with a template;

performing a wavelet comparison when the match between the depolarization and template exists; and using a result of the wavelet comparison and selecting a therapy and delivering the therapy it to the patient based on the result.

2. The method of claim 1 wherein the wavelet comparison comprising:
(1) transforming the digitized signals into signal wavelet coefficients;
(2) identifying higher amplitude ones of the signal wavelet coefficients;
(3) generating a match metric corresponding to the higher amplitude ones of the signal wavelet coefficients and a corresponding set of template wavelet coefficients derived from signals indicative of a heart depolarization of known type, and
(4) identifying the heart rhythms in response to the match metric.

3. The method of claim 1 wherein the maximum and the minimum values of the depolarization relate to a peak to peak amplitude.

4. The method of claim 1 wherein determining the match between the template and the depolarization occurs without performing a complete match between template and the depolarization.

5. The method of claim 1 further comprising:
determining if the absolute normalized minimum and the absolute normalized maximum values exceed a noise floor threshold.

6. The method of claim 1 further comprising:
assigning a timing number (t) to a template wherein a maximum being assigned a value of +1 and a minimum being assigned a value −1; and
assigning a timing number (t) to each depolarization wherein a maximum being assigned a value of +1 and a minimum being assigned a value −1.

7. The method of claim 6 further comprising:
determining if the timing number for the template matches the timing number for a depolarization.

8. The method of claim 7 further comprising:
comparing normalized peak to peak amplitudes of the template to the normalized peak to peak amplitudes of the depolarization.

9. The method of claim 8, further comprising storing a number of matches and mismatches between beats of a tachyarrhythmia episode and a template beat representing depolarization of a known type.

10. The method of claim 1, further comprising performing a set of sequential comparisons of a set of gross features between an episode beat and a template beat.

11. The method of claim 10 wherein the set of sequential comparisons is three.

12. The method of claim 10 wherein the set of gross features of each beat is designated as simple numbers designated at 0, +1, −1, the simple numbers representing a certain kind of relationship between maximum and minimum amplitudes of each beat, and their timing of occurrence within the beat signal.

13. The method of claim 12 wherein the set of gross features of each beat is derived by simple arithmetic operations involving maximum and the minimum amplitudes.

14. The method of claim 13 wherein the simple arithmetic operations consist essentially of subtraction and division.

15. The method of claim 1, further comprising:
determining whether a mismatch exists between the depolarization and the template;
classifying the between the depolarization and the template as different; and
proceeding automatically to one of comparing another pair of beats and delivering appropriate therapy.

16. The method of claim 15, wherein proceeding automatically to one of comparing another pair of beats and delivering appropriate therapy being based on a present number of matches or mismatches between the template and a set of depolarizations in an episode.

17. The method of claim 1, further comprising:
determining a match exists between all gross features of a signal compared to a template signal; and
performing a more detailed waveform comparison routines using wavelet analysis for a final determination of difference or similarity between the two beats.

18. An article comprising a non-transitory computer readable medium having instructions stored thereon, which when executed, causes:
sensing electrical signals associated with depolarizations of a patient's heart;
converting the sensed electrical signals to digital values and storing the digital values;
normalizing solely a maximum and a minimum value of the stored digital values associated with a depolarization of the patient's heart without normalizing other stored digital values of the depolarization;
comparing the maximum and minimum values associated with the depolarization to maximum and minimum values associated with a template derived from signals indicative of a heart depolarization of known type;
determining if a match exists between the maximum and minimum values associated with the depolarization to the maximum and minimum values associated with a template; performing a wavelet comparison when the match between the depolarization and template exists; and
using a result of the wavelet comparison and selecting a therapy and delivering the therapy it to the patient based on the result.

19. The article of claim 18 wherein the maximum and the minimum values of the depolarization relate to a peak to peak amplitude.

20. The article of claim 18 wherein determining the match between the template and the depolarization occurs without performing a complete match between template and the depolarization.

21. A method of classifying heart rhythms, comprising:
sensing electrical signals associated with depolarizations of a patient's heart;
converting the sensed electrical signals to digital values and storing the digital values;
normalizing solely a maximum and a minimum value of the stored digital values associated with a depolarization of the patient's heart without normalizing other stored digital values of the depolarization;
comparing the maximum and minimum values associated with the depolarization to maximum and minimum values associated with a template derived from signals indicative of a heart depolarization of known type;

determining if a match exists between the maximum and minimum values associated with the depolarization to the maximum and minimum values associated with a template;

performing a wavelet comparison when the match between the depolarization and template exists; and using a result of the wavelet comparison to classify the heart rhythms.

22. The method of claim 21 wherein the wavelet comparison comprising:
   (1) transforming the digitized signals into signal wavelet coefficients;
   (2) identifying higher amplitude ones of the signal wavelet coefficients;
   (3) generating a match metric corresponding to the higher amplitude ones of the signal wavelet coefficients and a corresponding set of template wavelet coefficients derived from signals indicative of a heart depolarization of known type, and
   (4) identifying the heart rhythms in response to the match metric.

23. The method of claim 21 wherein the maximum and the minimum values of the depolarization relate to a peak to peak amplitude.

24. The method of claim 21 wherein determining the match between the template and the depolarization occurs without performing a complete match between template and the depolarization.

25. The method of claim 21 further comprising:
determining if the absolute normalized minimum and the absolute normalized maximum values exceed a noise floor threshold.

26. The method of claim 21 further comprising:
assigning a timing number (t) to a template wherein a maximum being assigned a value of +1 and a minimum being assigned a value −1; and assigning a timing number (t) to each depolarization wherein a maximum being assigned a value of +1 and a minimum being assigned a value −1.

27. The method of claim 26 further comprising:
determining if the timing number for the template matches the timing number for a depolarization.

28. The method of claim 27 further comprising:
comparing normalized peak to peak amplitudes of the template to the normalized peak to peak amplitudes of the depolarization.

29. The method of claim 28, further comprising storing a number of matches and mismatches between beats of a tachyarrhythmia episode and a template beat representing depolarization of a known type.

30. The method of claim 21, further comprising performing a set of sequential comparisons of a set of gross features between an episode beat and a template beat.

* * * * *